United States Patent
Staker et al.

(10) Patent No.: US 9,880,089 B2
(45) Date of Patent: *Jan. 30, 2018

(54) HIGH-DENSITY DEVICES WITH SYNCHRONOUS TRACKS FOR QUAD-CELL BASED ALIGNMENT CORRECTION

(71) Applicant: Complete Genomics, Inc., Mountain View, CA (US)

(72) Inventors: Bryan P. Staker, San Ramon, CA (US); Paul Heilman, San Carlos, CA (US)

(73) Assignee: Complete Genomics, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/090,529

(22) Filed: Nov. 26, 2013

(65) Prior Publication Data

US 2014/0085457 A1  Mar. 27, 2014

Related U.S. Application Data (63) Continuation-in-part of application No. 13/222,925, filed on Aug. 31, 2011, now abandoned.

(60) Provisional application No. 61/378,848, filed on Aug. 31, 2010, provisional application No. 61/378,844, filed on Aug. 31, 2010.

(51) Int. Cl.
   *C12M 1/34*     (2006.01)
   *C07H 21/02*    (2006.01)
   *B01L 99/00*    (2010.01)
   *G01N 21/01*    (2006.01)
   *H04N 7/18*     (2006.01)
   *G01N 21/64*    (2006.01)

(52) U.S. Cl.
   CPC ......... *G01N 21/01* (2013.01); *G01N 21/6456* (2013.01); *H04N 7/18* (2013.01)

(58) Field of Classification Search
   None
   See application file for complete search history.

(56) References Cited

U.S. PATENT DOCUMENTS

| | | | |
|---|---|---|---|
| 6,210,891 B1 | 4/2001 | Nyren et al. | |
| 6,272,207 B1* | 8/2001 | Tang | 378/149 |
| 6,309,824 B1 | 10/2001 | Drmanac | |
| 6,376,177 B1* | 4/2002 | Poponin | C12Q 1/6825 |
| | | | 435/6.12 |
| 6,396,995 B1 | 5/2002 | Stuelpnagel et al. | |
| 6,401,267 B1 | 6/2002 | Drmanac | |
| 6,537,801 B1 | 3/2003 | Ida et al. | |
| 6,544,732 B1 | 4/2003 | Chee et al. | |
| 6,828,100 B1 | 12/2004 | Ronaghi | |
| 6,833,246 B2 | 12/2004 | Balasubramanian | |
| 6,864,052 B1 | 3/2005 | Drmanac | |
| 6,911,345 B2 | 6/2005 | Quake et al. | |
| 7,070,927 B2 | 7/2006 | Drmanac | |
| 7,072,500 B2 | 7/2006 | Cerrina et al. | |
| 7,230,705 B1 | 6/2007 | Yang et al. | |
| 7,422,911 B2* | 9/2008 | Schembri | B01J 19/0046 |
| | | | 435/287.2 |
| 8,175,452 B1 | 5/2012 | Staker et al. | |
| 8,298,768 B2 | 10/2012 | Drmanac | |
| 8,445,194 B2 | 5/2013 | Drmanac | |
| 8,774,494 B2 | 7/2014 | Staker | |
| 2001/0038070 A1* | 11/2001 | Hausch | C12Q 1/683 |
| | | | 250/288 |
| 2002/0102578 A1* | 8/2002 | Dickinson | B01J 19/0046 |
| | | | 435/6.11 |
| 2003/0036067 A1 | 2/2003 | Schwartz et al. | |
| 2004/0253614 A1* | 12/2004 | Yonekawa | B01L 3/50255 |
| | | | 435/6.11 |
| 2007/0087362 A1 | 4/2007 | Church et al. | |
| 2007/0207482 A1 | 9/2007 | Church et al. | |
| 2008/0234136 A1 | 9/2008 | Drmanac et al. | |
| 2008/0267022 A1 | 10/2008 | Bakker | |
| 2009/0017197 A1* | 1/2009 | Zhang | G01N 33/5438 |
| | | | 427/126.5 |
| 2009/0155793 A1 | 6/2009 | Oliphant | |
| 2009/0264299 A1 | 10/2009 | Drmanac et al. | |
| 2012/0224050 A1 | 9/2012 | Staker | |

FOREIGN PATENT DOCUMENTS

| | | |
|---|---|---|
| AU | 2011295903 | 3/2013 |
| AU | 2011295903 | 5/2015 |
| CA | 2809668 | 3/2012 |
| CN | 101466847 | 6/2009 |
| CN | 103180496 | 6/2013 |
| CN | 103180496 | 4/2015 |
| EP | 2611954 | 7/2013 |
| EP | 2611954 | 4/2015 |
| IN | 2331CHENP2013 | 2/2015 |
| JP | 2013536692 | 9/2013 |
| SG | 188311 | 4/2013 |
| SG | 188311 | 9/2015 |
| WO | 2005082098 | 9/2005 |
| WO | 2006073504 | 7/2006 |
| WO | 2012/031011 A1 | 3/2012 |

OTHER PUBLICATIONS

"Pixel," Wikipedia.com, accessed Jan. 11, 2017.*

(Continued)

*Primary Examiner* — Bradley L Sisson
(74) *Attorney, Agent, or Firm* — Kilpatrick Townsend & Stockton LLP (57) ABSTRACT

An array chip design is provided where the chip includes a field region arranged with sites according to a first pitch and at least one track region having a one-dimensional site pattern arranged according to a second pitch that is less dense and is an integer multiple of the first pitch so that observation through pixel-based sensors using one-dimensional quad-cell averaging can be applied in the track region, thereby to attain alignment of the chip to pixel-based optical instrumentation with a higher density of sites.

17 Claims, 6 Drawing Sheets

(56) References Cited

OTHER PUBLICATIONS

International Search Report and Written Opinion for PCT Patent Application No. PCT/US2011/50047 dated Jan. 5, 2012, 10 pages.
International Preliminary Report on Patentability for PCT Patent Application No. PCT/US2011/50047 dated Mar. 5, 2013, 7 pages.
Bajcsy, Peter, "Gridline: Automatic Grid Alignment in DNA Microarray Scans", IEEE Transactions on Image Processing, vol. 13, No. 1, Jan. 2004, pp. 15-25.
"Viruses" (Wikipedia.com, accessed Nov. 24, 2012) 34 pages.
"How many species of bacteria are there" Wisegeek.com; accessed Sep. 23, 2011, 2 pages.
"Plant" (Wikipedia.com; accessed Mar. 8, 2013) 12 pages.
"Mammal" (Wikipedia.com; accessed Sep. 22, 2011) 17 pages.
"Murinae" (Wikipedia.com, accessed Mar. 18, 2013) 21 pages.
Non-Final Office Action dated Dec. 3, 2012 for U.S. Appl. No. 13/222,925, 12 pages.
Final Office Action dated May 30, 2013 for U.S. Appl. No. 13/222,925, 22 pages.
Non-Final Office Action dated Jun. 18, 2014 for U.S. Appl. No. 13/221,648, 14 pages.
Bajcsy, et al., "Gridline; Automatic Grid Alignment in DNA Microarray Scans," IEEE Transactions on Image Processing, vol. 13, No. 1, Jan. 2004, pp. 15-25.
Extended European Search Report for European Patent Application No. 11822596.0 dated Mar. 27, 2015, 9 pages.
Gu Jian et al: "A new approach to fabricating high density nanoarrays by nanocontact printing", Journal of Vacuum Science and Technology: Part 3, AVS / AIP, Melville, New York, NY, US, vol. 26. No. 6, Nov. 3, 2008 (Nov. 3, 2008), pp. 1860-1865, XP012114385, ISSN: 1071-1023, DOI: 10.1116/1.2998754.
Office Action dated Aug. 27, 2015 for U.S. Appl. No. 13/221,648.
Australian Application No. 2011295903, First Examiner Report dated Apr. 1, 2014, all pages.
Australian Application No. 2011295903, Notice of Acceptance dated Apr. 24, 2015, all pages.
Chinese Application No. 201180050914.3, Office Action dated Oct. 17, 2014, all pages. (English translation by Insight Intellectual Property Attorneys).
Chinese Application No. 201180050914.3, Office Action dated Feb. 7, 2014, all pages. (English translation by Insight Intellectual Property Attorneys).
Japanese Application No. 2013-527283, Office Action dated Mar. 8, 2016, all pages. (English translation by Yamakawa International Patent Office.).
Japanese Application No. 2013-527283, Office Action dated Jul. 21, 2015, all pages. (English translation by Yamakawa International Patent Office.).
U.S. Appl. No. 13/221,648, Advisory Action dated Mar. 2, 2016, 4 pages.
U.S. Appl. No. 13/221,648, Final Office Action dated Feb. 26, 2015, 12 pages.
U.S. Appl. No. 13/221,648, Non-Final Office Action dated Jun. 24, 2016, 18 pages.
U.S. Appl. No. 13/221,648, Restriction Requirement dated Feb. 27, 2014, 7 pages.
U.S. Appl. No. 13/222,925, Restriction Requirement dated Aug. 31, 2012, 5 pages.

\* cited by examiner

$$\Delta x = (I_1 + I_3) - (I_2 + I_4)$$
$$\Delta y = (I_1 + I_2) - (I_3 + I_4)$$

HIGH-DENSITY DEVICES WITH SYNCHRONOUS TRACKS FOR QUAD-CELL BASED ALIGNMENT CORRECTION

PRIORITY CLAIM; CROSS-REFERENCES TO RELATED APPLICATIONS

This application is a continuation application of co-pending U.S. Ser. No. 13/222,925 filed Aug. 31, 2011 and claims priority and benefit under 35 U.S.C. §119(e) from U.S. Provisional Patent Application No. 61/378,848, filed on Aug. 31, 2010; this application also claims priority and benefit under 35 U.S.C. §119(e) from U.S. Provisional Patent Application No. 61/378,844, filed on Aug. 31, 2010.

This application is related to U.S. application Ser. No. 13/221,648, which was filed on Aug. 30, 2011.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND

This description relates to array chips used for analysis by optical techniques.

Array chips allow large numbers of observations to be performed in parallel. For example, an array chip may be part of a system for processing experiments in parallel. Array chips have solid, planar substrates made from silicon or glass wafers, or other materials. Markers are applied to array chips in regular patterns.

However, obtaining useful data form an image of a dense array chip is complicated by competing interests of spatial resolution, accuracy, and speed. Images must be obtained at high enough magnification for individual sites to be clearly resolved. At the same time images must cover a large enough field of view for sites to be correctly identified. Finally, for large scale studies, imaging and image processing must take place quickly enough to provide for sufficient throughput and to make operations commercially feasible.

SUMMARY

Array chips are provided that address the competing interests involved in imaging and image processing of elements disposed on the chips, such as biochemical assays involved in sequencing. For example, high-density array chips described herein address the problem of how to achieve a very high density of elements on the chips while at the same time allowing for rapid extraction of data from images of the chips. Further, the high-density array chips described herein also address the problem of how to provide for real-time alignment between an array chip and a pixel-based imaging instrument that is used to take the images of elements disposed on the chip. As illustrated by the various embodiments and principles described herein, these problems are addressed by encoding information on an array chip in the form of one or more track regions that have different pitch and/or different density than other regions of the chip.

For example, the high-density array chips described herein provide for track regions that occupy a small percentage of the total area of the chips, while the rest of the chips' area is occupied by regions having a different and/or more dense array grid. Information encoded as one or more track regions of an array chip is used in operation to reduce the time necessary to align an imaging instrument (e.g., such as a microscope camera) with the chip, while at the same time providing for real-time adjustment of such alignment. The real-time alignment of the imaging instrument is achieved by continuously monitoring for alignment errors based on information extracted from the images of the track region(s) on the array chip, and then correcting the alignment based on the alignment errors as the imaging instrument moves across the array chip and takes images of the biochemical experiments disposed thereon.

According to the principles and embodiments described herein, an array chip design is provided where the chip includes a field region arranged with element sites according to a first pitch and at least one track region having a one-dimensional spot pattern arranged according to a second pitch that is less dense and is an integer multiple of the first pitch but which is offset from tracks of the field region so that quad-cell alignment can be applied in the track region, thereby to attain alignment of the chip to optical instrumentation with a higher density of element sites.

In one aspect of this embodiment, the field region has a density of one object space pixel per one element site. In another aspect, the field region has a density of two object space pixels per one element site, the element sites being arranged in a checkerboard pattern. In yet another aspect, the field region has a density of four object space pixels per one element site.

In one aspect, selected ones of the alignment sites are omitted in accordance with a preselected pattern. In yet another aspect, selected ones of the alignment sites are omitted in accordance with a pseudo-random pattern.

In one aspect the single dimension, along which the track region is disposed, is a horizontal dimension. In another aspect the single dimension is a vertical dimension.

In one aspect, the track region is separated from the field region by a site-free band. In another aspect, the size of the track region is one of: four times the size of an object space pixel, and six times the size of an object space pixel.

In one aspect, the substrate of the array chip further comprises a horizontal track region that is disposed substantially perpendicular to the vertical track region, where the horizontal track region comprises track sites disposed according to the second patterned array along a second dimension that is substantially perpendicular to the single dimension, along which the track region is disposed.

In an example embodiment, a method comprises: an imaging instrument taking an image of a chip on which target elements have been disposed, where the chip comprises: a substrate comprising a field region and a track region, experiment sites disposed in a first patterned array that is defined by a first pitch and that is disposed in the field region, and alignment sites disposed in a second patterned array that is defined by a second pitch along a single dimension and that is disposed in the track region, where the second pitch differs from the first pitch by an integer multiple; an error-determination logic determining a correction alignment term for the single dimension by using, at least in part, quad-cell alignment based on signals recorded in the image of the alignment sites in the at least one track region; and automatically aligning the chip with the imaging instrument along the single dimension based on the correction alignment term.

In one aspect of this embodiment, the method further comprises the error-determination logic determining a second correction alignment term for a second dimension by using, at least in part, quad-cell alignment based on signals recorded in the of the alignment sites in the track region, where the second dimension is substantially perpendicular to the single dimension; and automatically aligning the chip with the imaging instrument along the second dimension based on the second correction alignment term.

In one aspect of this embodiment, the step of the error-determination logic determining the correction alignment term for the single dimension fighter comprises: as part of the correction alignment term, determining a whole-pixel misalignment error based at least in part on: the signals recorded in the image of the alignment sites in the track region, and information representing a pattern of deletion sites in the at least one track region.

In one aspect, a subset of the alignment sites in the track region is selectively omitted to form a pattern of deletions or deletion sites, and step of the error-determination logic determining the correction alignment term further comprises computing the correction alignment term based at least in part on an ordered data set that represents the pattern of deletions.

The invention can be better understood by reference to the following detailed description in connection with the accompanying drawings.

DETAILED DESCRIPTION

In the following description, for the purposes of explanation, numerous specific details are set forth in order to provide a thorough understanding of the present invention. It will be apparent, however, to the skilled in the art, that the present invention may be practiced without all or some of these specific details.

Selected Definitions

"Array chip" (or simply "chip") refers to a solid phase support (e.g., such as a substrate) having a surface, preferably but not exclusively a planar or substantially planar surface, that carries an array of element sites.

"Image space" refers to the area covered by the set of pixels in a camera, and "image space pixel" refers to a camera pixel.

"Logic" refers to a set of instructions which, when executed by one or more processors, are operable to perform one or more functionalities and/or return data in the form of one or more results. In various embodiments and implementations, any such logic may be implemented as one or more software components that are executable by one or more processors, as one or more hardware components such as Application-Specific Integrated Circuits (ASICs) and/or Field-Programmable Gate Arrays (FPGAs), or as any combination of one or more software components and one or more hardware components. The software component(s) of any particular logic may be implemented, without limitation, as a standalone or client-server software application, as one or more software modules, as one or more libraries of functions, and as one or more static and/or dynamically-linked libraries.

"Object space" refers to the area of an object such as an array chip, and thus "object space pixel" refers to a unit of area on an object such as an array chip. The size of object space pixels is typically determined by the size of the image space pixels (i.e., camera pixels) and the magnification that is applied when the camera is used to take images of the object space. The magnification is the ratio of the size of an image space pixel (i.e., a camera pixel) to the actual size of the object space area that corresponds to the image space pixel as observed by the camera. For example, a magnification of 16× allows a camera using 8 µm pixels to observe 500 nm object space pixels. In various embodiments, the size of an object space pixel may be between 200-1000 nm in width and 200-1000 nm in length; in a preferred aspect the size of an object space pixel may be 320 nm by 320 nm, more preferably 600 nm by 600 nm, even more preferably 500 nm by 500 nm. In some embodiments, the size of an object space pixel is selected to be substantially the same as, or slightly bigger, than the size of a site on an array chip, so that only a single discrete site will fit into an object space pixel. This ensures that, in operation, the intensity of the energy (e.g., light) emitted from a site on the array chip can be recorded by a single camera pixel.

"Pitch" (also referred to as "period") refers to a uniform distance that defines a pattern such as, for example, an array. The pitch of an array chip, or a region thereof, refers to the uniform distance between the centers of any two adjacent sites disposed in an array grid on the chip, thereby defining the array of the chip, or the region thereof. The pitch of a camera refers to the uniform distance between the centers of any two adjacent camera pixels and defines the pixel array of the camera.

"Site" (also referred to as "spot") refers to a spatially defined area on an array chip that does not overlap with other sites on the chip; that is, the sites on an array chip are spatially discrete and may be arranged in a particular pattern. On an array chip, a site is typically configured to have dimensions (e.g., length, width, and possibly depth) that are suitable for the attachment of nucleic acids or macromolecules. Examples of sites include, but are not limited to, depressions, raised areas, micro-wells, beads, and the like.

Array Chip Imaging

Image-based techniques identify individual elements on an array chip by the positions of the sites on which the elements are disposed on the chip. For example, the intensity of the energy (e.g., such as light) emitted from the elements at the sites is recorded as an image, and the image is then processed to determine the positions of the sites on the chip. An element may be identified by the coordinates of its site on the chip in a two-dimensional (e.g., X-Y), planar coordinate system, for instance. An image of an array chip typically includes a large enough area such that locations of the elements' sites may be measured and/or computed with respect to the coordinate system in use. Some prior approaches use conventional alignment marks (e.g., such as cross etchings) for this purpose; however, drawbacks of such marks include difficulty of observing them with fluorescence microscopes, incompatibility of materials, and wasted chip area. In contrast, the high-density array chips described herein use the elements themselves (as arranged in specific patterns), and the energy emitted therefrom, to aid identification.

In various operational contexts, images of the elements disposed on an array chip may be obtained with an imaging instrument that includes a camera attached to a fluorescence microscope. The magnification of the microscope determines how many element sites can be "seen" by a camera pixel at the one time; equivalently, the magnification determines the ratio of the size of a camera pixel (in image space) to the size of a chip area (in object space) that is observed and corresponds to the camera pixel. For example, a magnification of 16× allows a camera using 8 μm pixels to record signals from 500 nm chip areas (e.g., Object space pixels). Thus, the rate at which data may be extracted from an array chip depends, in part, on how many camera pixels correspond to each spot on the chip (presuming that a spot is entirely contained in an object space pixel). For example, a one-megapixel camera operating at twenty camera pixels per spot can image 50,000 spots. If the same camera is operated with two (or even one) camera pixel per spot, the number of spots per image is ten for twenty) times greater. While low pixel-to-spot ratios (e.g., such as 1:1, 2:1, and 4:1) are very desirable since they greatly increase imaging throughput, they also impose very demanding requirements on the alignment of the camera pixels with the array chip spots during operation.

According to the principles and embodiments described herein, carefully designed spatial patterns of sites for elements on an array chip aid the accuracy and speed of data acquisition via imaging. The specific layout principles described hereinafter enable rapid imaging of very high density arrays and thus improve the throughput of large scale imaging systems. Further, the described novel chip designs aid accuracy of chip alignment and identification while maximizing the area of the chip that can be used for element sites.

As described herein, precise alignment correcting for fractional offsets is achieved by correcting for errors in sub-pixel X-Y alignment by use of quad-cell minimization techniques. For the purposes of quad-cell techniques, magnification is intentionally set so that the period of the object space pixels corresponding to the pixels of the imaging element (e.g., a camera) is an integer multiple of the period that defines the track sites in a track region of the chip, and the track sites are disposed on the intersections of object space pixel boundaries. Accurate pixel-level alignment is achieved by providing for pre-defined and pseudo-randomly disposed sets of sites (herein referred to as deletion sites or reserved sites), on which materials are prevented from attachment to the chip substrate so that the sites appear to have been omitted. Thus these deletion sites of the array can be used in a pattern matching scheme as registration markers for absolute location identification.

High-Density Array Chips with Track Regions

Figure 1:
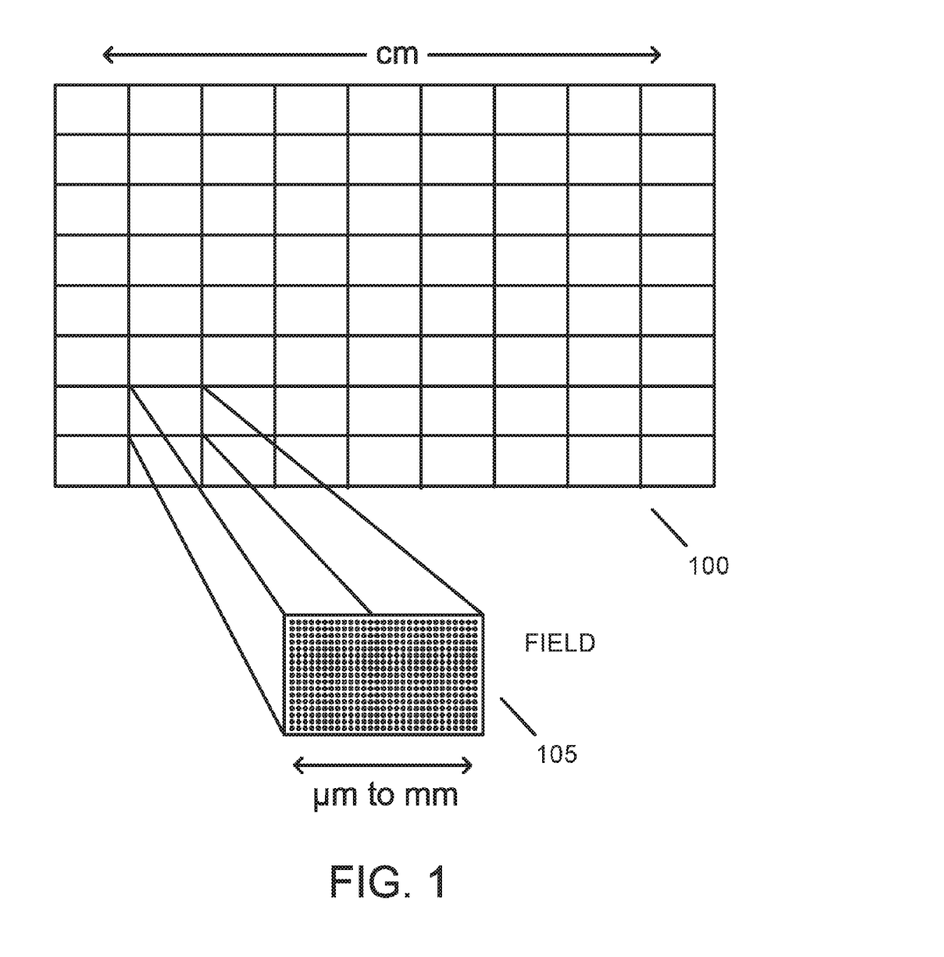
FIG. 1 is a top plan view of a portion of an array chip with an inset using an example pattern for field regions and track regions (size not to scale).

Turning now to FIG. 1, a high-density array chip according to one embodiment is shown. Chip 100 is based on a solid, planar substrate and is conveniently dimensioned in several centimeters in length and width. Typical chip dimensions may be 2.5 cm by 7.5 cm by 0.1 cm, for example. Smaller chips (e.g. less than about 0.5 cm on a side) are possible but may be less convenient to handle in some operational contexts, and it may be difficult to maintain required flatness for large chips (e.g., more than about 10 cm on a side). In some embodiments, chips designed according to the principles described herein may support more than one billion elements.

To break the imaging problem into manageable chunks, array chips are divided into micron-to-millimeter sized fields; e.g. field 105. In one embodiment, a typical field may be 500 μm by 500 μm; thus a typical chip is divided into hundreds or thousands of fields. In other embodiments, a field may be of sizes that are between 320-1600 μm by 320-1600 μm, 600 μm by 600 μm, or even 1.6 mm by 700 μm.

Figure 2:
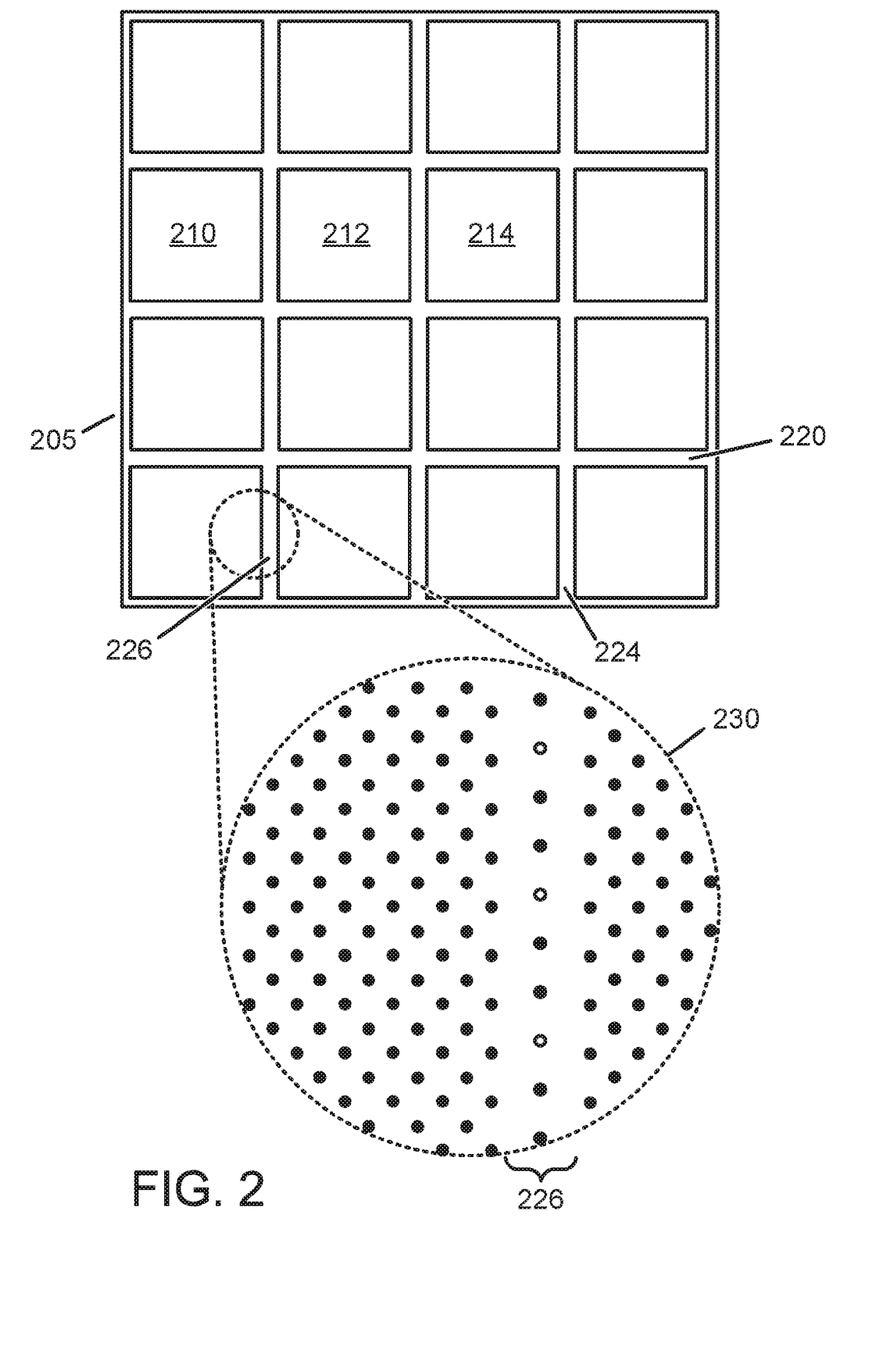
FIG. 2 is a top plan view of one field of an example array chip with an inset showing details of a part of a subfield region and one track region (size not to scale).

FIG. 2 is a diagram of one field 205 of a high-density array chip. The field is divided into subfields (e.g. 210, 212, 214) separated by track regions that are aligned substantially along a horizontal X dimension (e.g., track region 220) and by track regions that are aligned substantially perpendicular to the X dimension along a vertical Y dimension (e.g., track regions 224, 226). A magnified view 230 shows spots in two subfields separated by track region 226. The chips of FIGS. 1 and 2 do not include any marks or features used for alignment other than track regions that separate the subfields. Properties of the track regions, principles by which they are laid out, and their relationship to the subfields are discussed in detail below.

Figure 3:
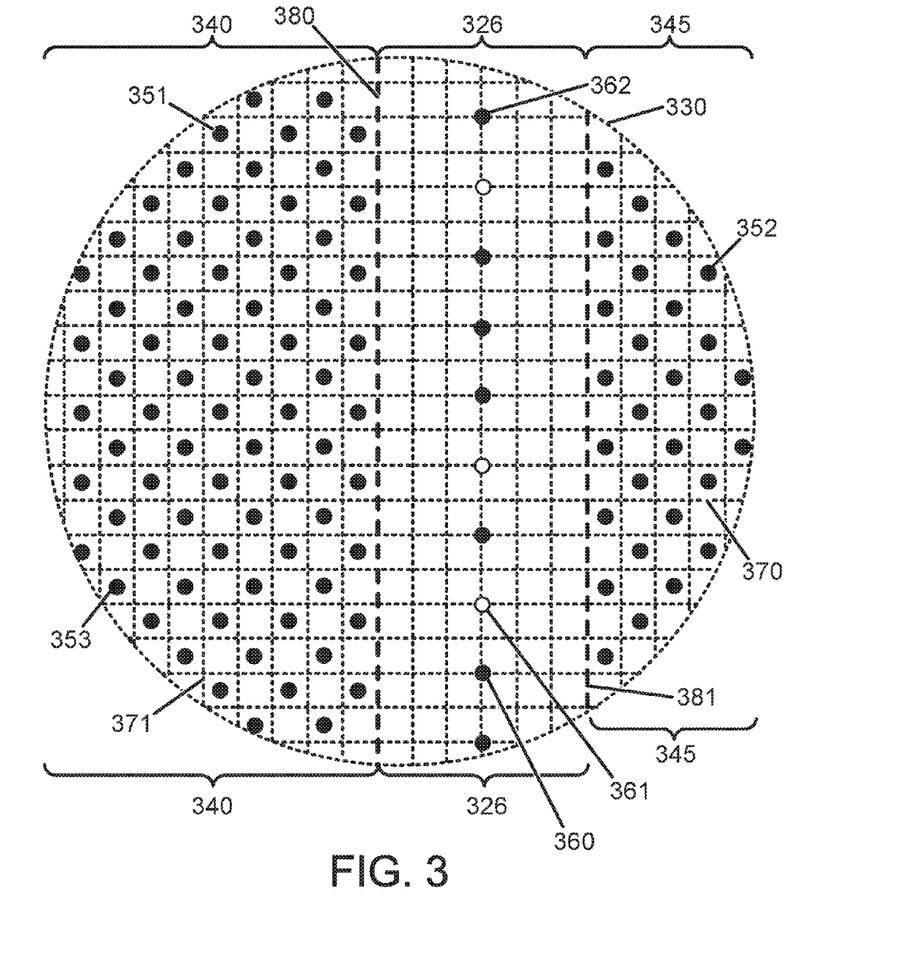
FIG. 3 is a top plan view of part of a subfield of one field region and one track region of an example high-density array chip illustrating one embodiment of a layout pattern of sites relative to an overlay of object space pixels showing relative scale and position.

FIG. 3 is a diagram of part of a subfield of one field of a high-density biochemical array chip according to an example embodiment. The circular area 330 represents the same magnified view of a field as view 230 in FIG. 2. In this view, for illustration purposes only, track region 326 is bounded by heavy dashed lines 380 and 381; in practice, however, such dashed lines are not present on the array chip itself.

In the embodiment illustrated in FIG. 3, the width of vertical track region 326 is set to equal the length of 6 object space pixels, which correspond to camera (or image space) pixels according to the applicable magnification. In this embodiment, the height of a horizontal track region may be the same as the width of track region 326. In some embodiments, the width of a vertical track region (and similarly, the height of a horizontal track region) may be equal to 4 object space pixels in the array grid of the adjacent non-track regions. As illustrated in FIG. 3, a site-free band separates track region 326 from each of the adjacent regions 340 and 345. In operation, these site-free bands prevent the light signals, emitted from the experiments disposed on the more densely populated regions 340 and 345, from interfering with the signals emitted from the experiments disposed on the sites of track region 326. In other embodiments, the track region does not need to be separated from the field regions with site-free bands; rather, in these embodiments a correlator logic may be used to correctly process the signals recorded in an image of the track region even if the track region is embedded into a field region without a separation site-free band.

In the embodiment of FIG. 3, regions 340 and 345 are parts of adjacent subfields on either side of track region 326. Fluorescent spots (e.g. 351, 352, and 353) may appear in the subfields. Fluorescent spots (e.g. 360, 362) are also to be seen in the track region 326. In this embodiment, there is no difference in the elements disposed on subfield spots and track spots, or in the fluorescent markers used to see them. Open circles (e.g. 361) represent the intentional absence of a spot, e.g., a deletion site and more specifically a deletion spot. Such deletion spots are conveniently made by omitting and in effect deleting corresponding features on a photolithography mask used to pattern the sites on an array chip. According to the principles described herein, the deletion spots preferably account for more than about 5% of the available locations in the track region but less than about 15%. The spots in the track region may be attachment sites for fluorescent molecules, the same or similar to sites in the field region. The deletion spots may be the absence of attachment sites, or they may be attachment sites that have been subsequently chemically treated to inhibit or prevent binding with molecules.

For illustration purposes only, light dashed lines (e.g. 370, 371) in FIG. 3 indicate the boundaries between the object space pixels that correspond to the boundaries of the physical pixels (e.g., the image space pixels) in a digital camera that is used to image the chip at a specific magnification. Thus, while FIG. 3 is drawn at a resolution much finer than a camera's pixel period, an image of region 330 taken with a camera having pixels bounded by the light dashed lines in the figure could not resolve spatial features finer than the pixel period. Despite this limitation, the layout of spots in the track regions permits alignment of spots to pixels with sub-pixel resolution as described below.

The layout of spots on the chip shown in FIG. 3 (and therefore the layout of the elements on the chip in operation) provides for a two-to-one ratio of object space pixels to array spots in regions 340 and 345 that are part of subfields on the array chip. That is, the area in regions 340 and 345 is configured at a density of two object space pixels per one array spot. To the extent that track regions take up only a few percent of the total area of a field, the two-to-one pixel to spot ratio holds approximately for an entire chip. Higher density layouts are possible, however, as further described below. Significantly, the track spots 360, 361, 362, etc., in the track region 326 are spaced at a pitch that is synchronized with the spacing of field spots 351, 352, 353, etc., in the field regions 340, 345, except that the pitch of the track spots is offset from the pitch of the field spots by one half of an object space pixel.

For example, FIG. 3 illustrates an array chip in which the spots in the subfield regions are disposed on an array in a checkerboard pattern. An array with a checkerboard pattern has a spot pitch of $$\sqrt{2}*\text{the array pitch},$$

and it is the diagonal distance between the centers of any two adjacent spots. For example, for an array with an object space pitch of 500 nm, the spot pitch defining a checkerboard pattern would be $$\sqrt{2}*500=702 \text{ nm}.$$

Viewed in another way, in an array with spots arranged in a checkerboard pattern, the spots in each adjacent row are offset by ±1 column.

In fluorescent imaging, using a checkerboard pattern on an array chip helps because light from a chip spot may typically bleed horizontally or vertically across to adjacent spots but not to corner spots. Thus, disposing the spots of an array chip in a checkerboard pattern allows for the very high density of two object space pixels (and, therefore, two camera pixels) per one spot while at the same time minimizing the cross-talk from signal bleeding within the electronics of the imaging instrument.

Figure 4:
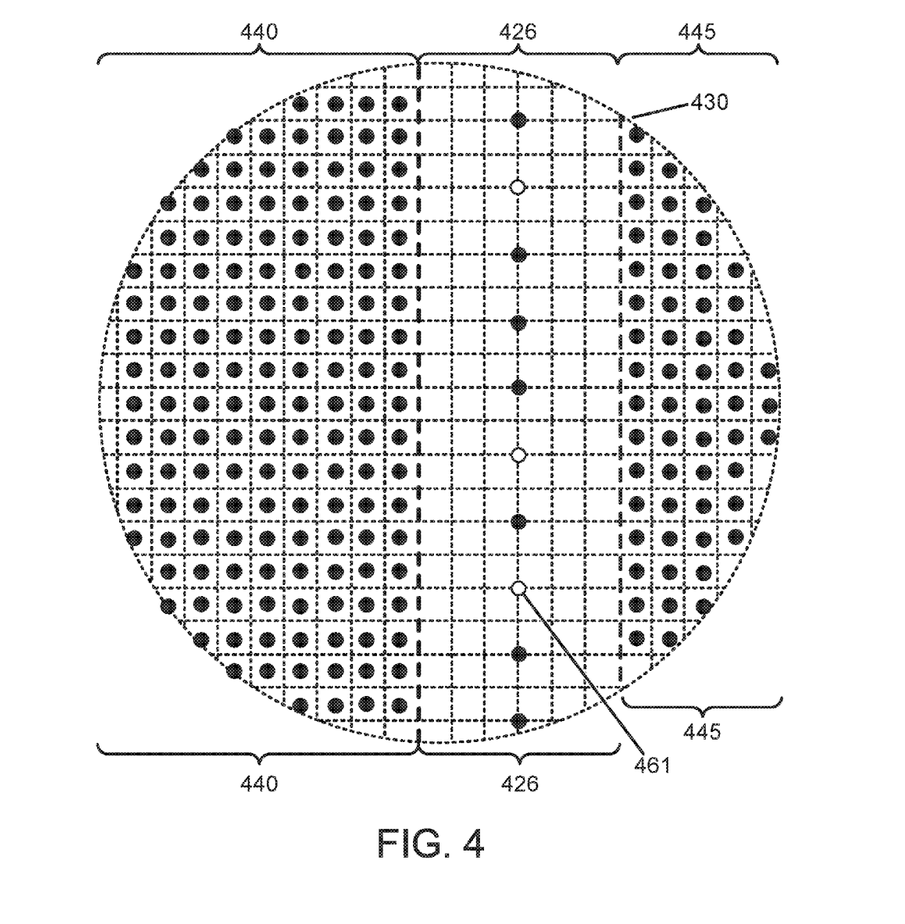
FIG. 4 is a top plan view of part of a subfield of one field region and one track region of an example high-density array chip illustrating another embodiment of a layout pattern of attachment sites relative to an overlay of object space pixels showing relative scale and position.

FIG. 4 is a diagram of part of a subfield of one field of a high-density array chip according to an example embodiment. FIG. 4 is similar to FIG. 3, including that the spots in the field region are synchronous with spots in the track region, but in FIG. 4, the object space pixel (and, therefore, the camera pixel) to spot ratio is one-to-one in the subfields. Circular area 430 represents the same magnified view of a field as view 230 in FIG. 2 and view 330 in FIG. 3. In this view, for illustration purposes only, track region 426 is bounded by heavy dashed lines; in practice however, such dashed lines are not present on the array chip itself.

In the embodiment illustrated in FIG. 4, the width of vertical track region 426 is set to equal the length of 6 array (or object space) pixels, which correspond to camera (or image space) pixels according to the applied magnification. In this embodiment, the height of a horizontal track region on the array chip may be the same as the width of track region 426. In other embodiments, the width of a vertical track region (and similarly, the height of a horizontal track region) may be equal to 4 object space pixels in the array grid of the adjacent non-track regions. As illustrated in FIG. 4, a site-free band separates track region 426 from each of the adjacent regions 440 and 445. In operation, these site-free bands prevent the light signals, emitted from the experiments disposed on the more densely populated regions 440 and 445, from interfering with the signals emitted from the experiments disposed on the sites of track region 326. In other embodiments, the track region does not need to be separated from the field regions with site-free bands; rather, in these embodiments a correlator logic may be used to correctly process the signals recorded in an image of the track region even if the track region is embedded into a field region without a separation site-free band.

Regions 440 and 445 are parts of adjacent subfields on either side of track region 426. Fluorescent spots (shown as black dots) appear in the subfields and in the track region. Open circles (e.g. 461) represent the intentional absence of a spot (e.g., a deletion spot). Such deletion spots may be conveniently made by deleting corresponding features on a photolithography mask used to pattern the sites on an array chip. According to the principles described herein, the deletion spots preferably account for more than about 5% of the available locations in the track region but less than about 15%. The spots in the track region may be attachment sites for molecules, the same or similar to sites in the field regions. The deletion spots may be the absence of attachment sites, or they may be attachment sites that have been subsequently chemically treated to inhibit or prevent binding with molecules.

The layout of spots shown in FIG. 4 provides for a one-to-one ratio of object space pixels (and, therefore, camera pixels) to array spots in regions 440 and 445 that are part of subfields on the array chip. That is, the area in regions 440 and 445 is configured at a density of one object space pixel (and, therefore, one camera pixel) per one array spot. This layout leads to a very large amount of information contained in each field image. For example, in the embodiment illustrated in FIG. 4, approximately 5% of the chip area is used for track regions and the remaining 95% percent of the chip area is used at maximum density of one object space pixel (and, therefore, one camera pixel) per one array spot.

In other embodiments according to the principles described herein, the sites in the non-track regions of an array chip may be disposed in a layout that provides a density of 4 object space pixels (and therefore, 4 camera pixels) per one site. Even though such 4:1 pixels-per-site density is lower than the site densities illustrated in FIG. 3 and FIG. 4, it is still a very high density when compared with the densities of conventional array chips; at the time of filing of the present application, commercially available biochemical array chips have densities in the range of 110:1 to 25:1 pixels-per-site density.

The design of the high-density array chips described herein leaves little room for imaging error because misalignment of camera pixels and array spots of as little as one quarter pixel period (0.25) can lead to unacceptable data acquisition errors. To address this, described below are techniques for designing array chips with track regions that support correction of alignment errors by using quad-cell based alignment.

Quad-Cell Based Alignment Correction

The track regions of the high-density array chips described herein (e.g., as illustrated it FIG. 3 and FIG. 4) are designed such that an imaging system can use them for several simultaneous operations: (1) alignment of fields with sub-pixel precision; and (2) absolute location of spots in a pixel coordinate system. Principles underlying the first of these operations, alignment of fields with sub-pixel precision, are discussed in connection with FIG. 5.

Figure 5:
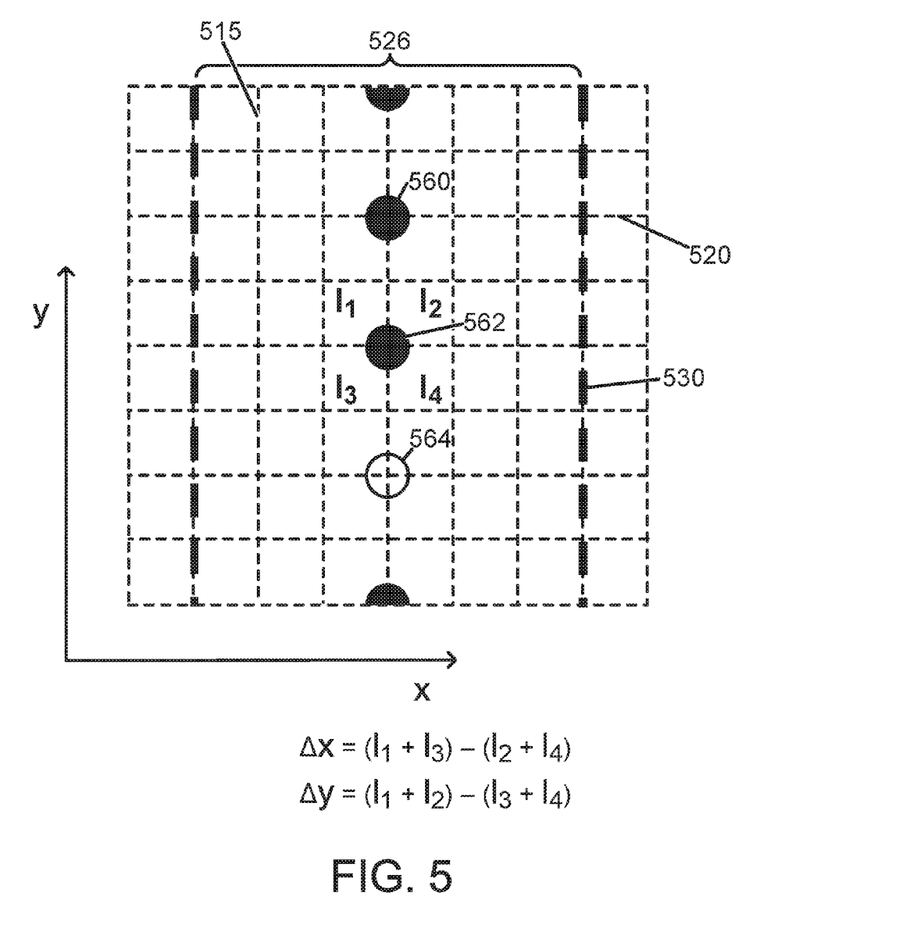
FIG. 5 is a detail of a portion of a track region as in FIG. 4 for illustrating quad-cell alignment techniques.

FIG. 5 is a detail of a portion of FIG. 4 for illustrating quad-cell alignment techniques. FIG. 5 shows a small section of a track region 526 of a chip. Light dashed lines (e.g. 515, 520) show the boundaries between object space pixels that correspond to the boundaries of the physical pixels (e.g., image space pixels) in a camera that is used to image the chip at a specific magnification, while heavy dashed lines (e.g. 530) mark the boundary between the subfield regions and the track region. (It is noted that the light dashed lines 515, 520 and the heavy dashed lines 530 are included in FIG. 5 for illustration purposes only; in practice, such dashed lines are not present on the array chip itself.)

Field spots in FIGS. 3 and 4 (e.g. 351, 352, and 353) are repeated in the X and Y directions with a period $\lambda_F$, where $\lambda_F$ is the period for field spots. Track spots (e.g. 360, 361, and 362) are repeated in the Y direction with a period $\lambda_T$, where $\lambda_T$ is the period for spots in the track region. (Deletion spots, drawn as open circles (e.g. 361), are included when measuring spot repetition period.) There is an integer-multiple relationship between $\lambda_F$ and $\lambda_F$; i.e. $\lambda_T = n \lambda_F$ where n is an integer. In addition, as part of manufacturing the array chip, the track spots in the chip are offset from the field spots, in both the X and Y dimensions, by the size of a half of an object space pixel. Thus, the track spots lie on the intersections of object pixel boundaries and effectively straddle four object space pixels. This fixed, and synchronous, relationship between field spots and track spots may be easily seen in FIGS. 3, 4, and 5 as the track spots all lie on object space pixel boundaries spaced two pixels apart (e.g., such as track spots 360, 361, 362, 461, 560, 562, 564).

When the period of field spots is the same as, or an integer multiple of the object space pixel period that corresponds (under the applied magnification) to the pixel period in a camera used to image a chip, careful layout of track spots such that they appear on the intersections of object space pixel boundaries increases the ability to accurately align a camera with the spots on the chip during operation. If the track spots were manufactured to appear at the center of object space pixels (which correspond to camera pixels), errors of as much as $$\frac{\lambda_P}{\sqrt{2}}$$

(where $\lambda_p$, the object space pixel period, is equal to or an integer sub-multiple of $\lambda_p$) could result.

In FIG. 5 track region 526 is bounded by heavy dashed lines. Spots in the track region 526 include spots 560 and 562. Reference numeral 564 indicates a deletion spot. FIGS. 3, 4, and 5 illustrate that "synchronized" track spots fall on the intersection of object pixel boundaries, and thus cover portions of the area of Ebur object space pixels, while field spots are manufactured to be substantially disposed on object space pixel centers. Said another way, "synchronized" track spots are laid out with the same period as field spots, but offset by half an object space pixel period in both X and Y dimensions, and thus effectively straddle four object space pixels. This property can facilitate the use of a so-called "quad-cell" error detection scheme by using differential measurements of recorded camera pixel intensities. In particular, alignment errors in the X and Y dimensions ($\Delta x$ and $\Delta y$, respectively) for each track spot may be calculated, as shown in FIG. 5, from the following two equations:

$$\Delta x_i = (I_1 + I_3) - (I_2 + I_4) \quad (1)$$

$$\Delta y_i = (I_1 + I_2) - (I_3 + I_4) \quad (2)$$

where $I_1$, $I_2$, $I_4$, and $I_4$ are the intensities recorded during operation, in an image of the chip, by the four pixels straddled by a particular track spot i as shown in FIG. 5. Sub-pixel alignment may be achieved based on the sub-pixel error that is computed by minimizing $\Delta x$ and $\Delta y$ as given above for all track spots simultaneously.

Thus, the location of the track spots may be determined with sub-pixel precision using quad-cell techniques, as further described below.

The operation for determining the absolute location of spots in a pixel coordinate system can be performed based on the information encoded in the layout of spots in the track region as follows. If the position of the track spots is known, the position of field spots may be calculated based on the known layout of subfield spots and track region spots on an array chip. The position of track spots may still be subject to offset errors of integer numbers of track spot periods, however. That is, during operation the camera pixels may be aligned with the object space pixels with sub-pixel precision, as described above, but there may still be misalignment by one or more pixels such that a particular camera pixel is aligned with the wrong object space pixel. Such "modulo one" track spot pitch ambiguities may be resolved through the use of omitted track spots, such as deletion spot 564 in FIG. 5.

Figure 6:
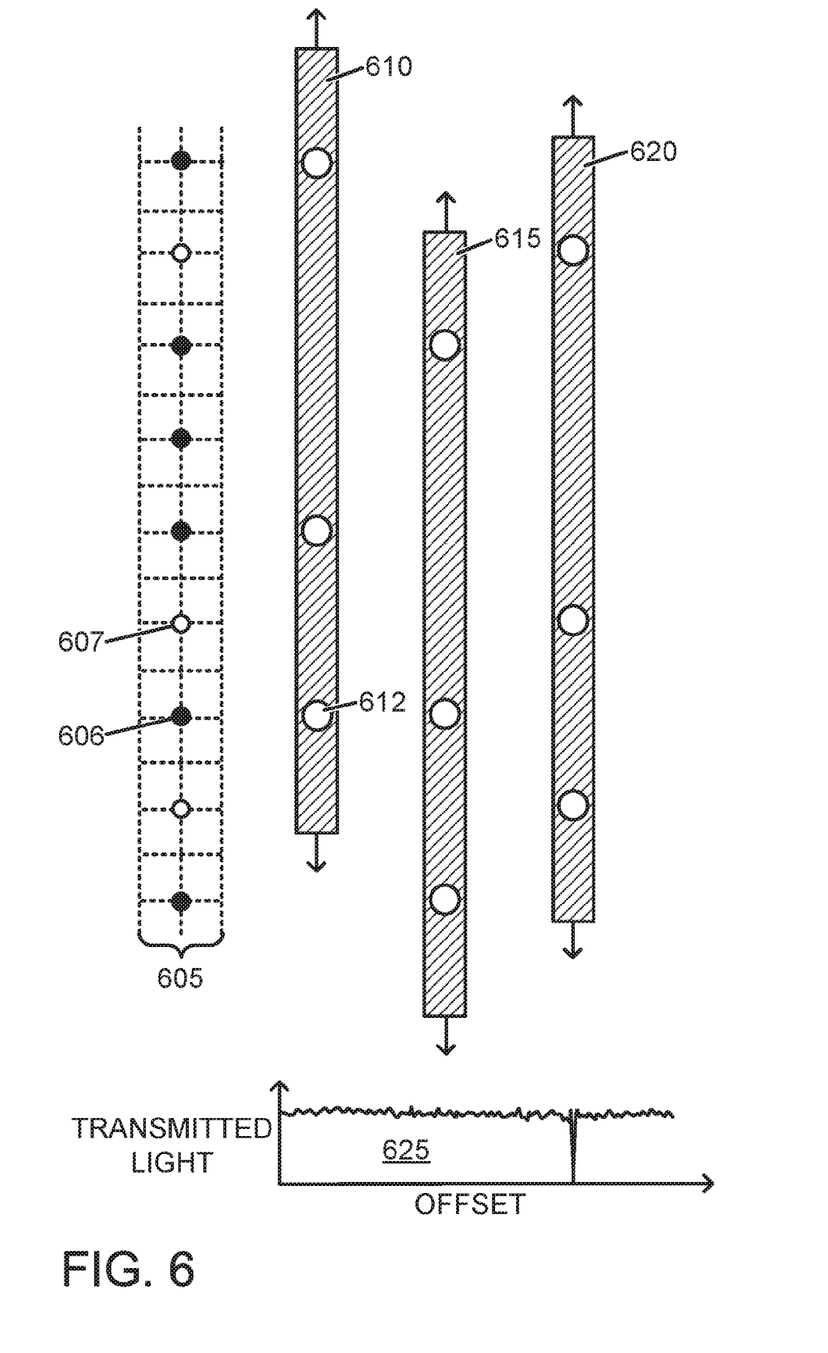
FIG. 6 is a diagram for illustrating offset determination using deletion patterns.

The absolute location of track spots (and therefore field spots fixed relative to the track spots when the array chip is manufactured) may be determined by analysis of track spot deletion patterns along the axis of the track regions, as illustrated in FIG. 6. In FIG. 6, track region 605 has both regular illuminated spots (e.g. 606) and deletion spots (e.g. 607), corresponding to active and deletion sites, respectively, on a chip in operation. For illustration purposes, masks 610, 615 and 620 are provided as aids to conceptualization of cross correlating a known deletion pattern with an image of track spots. Masks may be analytical rather than physical entities, namely, analytical indices of the location of expected deletion sites. Masks 610 and 615 are misaligned (by plus or minus one spot) while mask 620 is aligned with the deletion pattern of three consecutive deletion sites. When misaligned mask 610 or 615 is superposed with track region 605, light is transmitted through transparent openings such as at mask opening 612. On the other hand, when mask 620 (which is correctly aligned with the deletion pattern of track 605) is superposed with track region 605, very little light passes through its transparent openings as they line up with deleted spot locations. Graph 625 shows transmitted light versus offset during cross correlation of a mask pattern with an image of a track region encoded with a deletion pattern. The intensity of transmitted light drops sharply when the mask and track region are at the proper offset with respect to one another. This correlation property of masks with deleted spots is used in practice by a correlation logic that is configured to take as input an ordered data set representing the intensities recorded from the track spots and an ordered data set representing the mask of deleted spots (which is known and fixed relative to the object-space pixel coordinate system), and to generate as output an alignment error term that specifies the offset of the track spots (in whole pixels) from their correct location in the pixel coordinate system.

If the deletion pattern for a track region is pseudo-random, then the pattern has a wide spatial range; e.g. only one peak will appear in a cross correlation of the pattern and an image of the track region. If the deletion pattern is periodic, or partly so, more than one peak may appear in a cross correlation. Thus, pseudo-random deletion patterns are the most robust when the position of a track must be identified with no a priori information. On the other hand, initial rough alignment may be good enough that deletion patterns are not required to be strictly pseudo random.

Example Method of Using Quad-Cell Based Alignment Correction

In operation, when target nucleic acids are disposed on an array chip, a quad-cell based mechanism can be used to calculate the correction alignment term and to apply this term during the process of initial chip registration and during the process of continuously taking images of the chip (e.g., in a feed control that continuously corrects the alignment of the imaging instrument during imaging). The correction alignment term, $E_T$ for a single dimension (such as an X dimension or a Y dimension), is expressed as follows:

$$E_T = \lambda_T * e_d + e_{sp} \quad (3)$$

where $E_T$ is the correction alignment term for the specific single dimension, $\lambda_T$ is the pitch of sites in the track region along the single dimension, $e_d$ is the whole-pixel (track pitch) misalignment error that is an integer value indicating whole pixels, and $e_{sp}$ is the sub-pixel error determined by quad-cell based techniques. The size of the sub-pixel error, $e_{sp}$, less than the size (length or width) of an object space pixel as expressed by the following inequality $$-\frac{\lambda_T}{2} < e_{sp} < \frac{\lambda_T}{2}$$

where is $\lambda_T$ the pitch of sites in the track region along a single dimension (e.g., the X dimension or the Y dimension). Since in practice correction alignment may be needed both in the X dimension and the Y dimension, a first correction alignment term is computed for the X dimension and a second correction alignment term is computed for the Y dimension. The two correction alignment terms are then both applied in order to achieve the desired alignment between the camera pixels and the spots on the array chip.

In an example embodiment, a method for aligning an array chip comprises several steps. In the first step, an image of the sites in a track region is taken, and the signal intensities recorded in the image are converted into a data set. For example, the camera in an imaging instrument may snap one or more images of a track region, and an image processing logic may generate an ordered data set (referred to herein as "track site data set") that represents (e.g., as a linear profile) the intensities and positions of signals emitted from the track sites.

In the next step, the track site data set is passed through a filter and the pixel positions of the track sites with respect to the object space pixel coordinate systems are determined. Using quad-cell based techniques, the sub-pixel errors for both the X dimension and the Y dimension are determined by minimizing equations (1) and (2) across all track sites represented in the track site data set. For example, in one embodiment, an error-determination logic may Obtain the sub-pixel error in the X dimension, $\Delta x$, based on the following equation $$\Delta x = \frac{\sum_{i=1}^{N}(\Delta x_i)}{N},$$

in which N is the number of track sites for which at least one pixel intensity recorded in the image, and $\Delta x_i = (I_1^i + I_3^i) - (I_2^i + I_4^i)$, where $I_1^i$, $I_2^i$, $I_3^i$, and $I_4^i$ are the intensities of the four pixels surrounding track site i. Similarly, the error-determination logic may obtain the sub-pixel error in the Y dimension, y, based on the following equation $$\Delta y = \frac{\sum_{i=1}^{N}(\Delta y_i)}{N},$$

in which N is the number of track sites for which at least one pixel intensity is recorded in the image, and $\Delta y_i = (I_1^i + I_2^i) - (I_3^i + I_4^i)$, where $I_1^i$, $I_2^i$, $I_3^i$, and $I_4^i$ are the intensities of the four pixels surrounding track site i. This type of quad-cell mechanism determines the sub-pixel error for the entire track region along each of the X and Y dimensions and, therefore, also determines the sub-pixel error for the field regions of the chip, which are fixed relative to the track region when the chip is manufactured.

In the next step, the track site data set is correlated to ordered data sets representing (e.g., as linear profiles) one or more patterns of deletion spots in the track regions (referred herein as the deletion data sets). The correlation returns the whole-pixel misalignment error for the particular dimension along which the track region is disposed. For example, a correlation logic may take as input the track site data set and the deletion data sets. The correlation logic then compares the track site data set and the deletion data sets to determine that one deletion data set which most closely matches to the track site data set. The correlation logic then computes the whole-pixel misalignment error as the offset between the track site data set and the matching deletion data set. The operations in this step may be performed separately for the X dimension (on a track site data set representing a track region in the horizontal X dimension) and for the Y dimension (on a track site data set representing a track region in the vertical Y dimension) to determine the whole-pixel alignment error for the X dimension and the whole-pixel alignment error for the Y dimension, respectively.

In the next step, equation (3) above is used to determine the correction alignment term for each of the X dimension and the Y dimension based on the pitch of the sites in the track regions (which is known), the sub-pixel error computed for the track region along the appropriate (X or Y) dimension, and the whole-pixel alignment error computed for the track region along the appropriate (X or Y) dimension. For example, an error-determination logic may use equation (3) and the computed sub-pixel error and whole-pixel alignment error to calculate the correction alignment term for the track region along the X dimension, and the correction alignment term for the track region along the Y dimension.

In the final step, the camera pixels and the array grid of the array chip may be aligned by the amount of the correction alignment terms for the X dimension and the Y dimension. For example, a lateral offset system in the imaging instrument may adjust a galvo to shift the position of images in the camera based on the correction alignment term for the X dimension. A time-delay integration (TDI) offset system in the imaging instrument may adjust the pulse timing of the camera based on the correction alignment term for the V dimension.

The principles of designing the layout of track sites and the quad-cell based alignment described herein may be used in various methods at various stages in the examination of biochemical experiments disposed on an array chip. For example, in some embodiments, quad-cell alignment based on track region information as described herein may be used to align an array chip during the process of initial chip registration when the chip is affixed in a machine stage prior to imaging.

In other embodiments, the quad-cell alignment based on track region information as described herein may be used in a feed-forward control loop during the process of continuously taking images of the chip, where the alignment of the imaging instrument is corrected after taking each scan of the chip. For example, since scanning two adjacent columns of a chip results in negligible error offsets (e.g., 10-20 nm or less), the X and Y correction alignment terms can be accumulated across scans without losing significant alignment accuracy. Thus, after scanning a column and calculating its X and Y correction alignment terms, a feed-forward logic may add these two terms to the corresponding correction alignment terms that have been accumulated for the previously-scanned columns. In this manner, the correction alignment terms for the X and Y dimensions for a currently scanned chip column are used to adjust the imaging instrument before the next chip column is scanned, thereby achieving a feed-forward alignment.

In summary, the layout of a high-density array chip affects the rate of experimental data that may be extracted from the chip. A high density of experiments may be achieved by matching the imaged repetition period of elements to the pixel period (or a small integer multiple of the pixel period) of a camera. Data acquisition speed depends on alignment, absolute location, and identification of features in elemental images obtained, for example, by fluorescence microscopy. A chip layout with synchronous tracks enables precise alignment. Quad-cell based alignment may be used with synchronous tracks to determine sub-pixel alignment, while track deletion patterns facilitate resolution of modulo one errors that may be used for precise whole-pixel alignment.

An example embodiment of an array chip with track regions as described herein allows a machine to extract the location of a snapped image with respect to the array chip at least as fast as the machine is taking the images. For example, in a machine comprising two cameras that are taking images of an array chip at a rate of 30 frames per second (fps) each, 1000 images come through the machine every 15 seconds. By using array chips with track regions as described herein, the machine (or a component thereof) can determine the X-Y location of each image with respect to the chip within 15 milliseconds or less.

Array Chip Construction

In some embodiments, array chips are constructed by disposing one or more layers (e.g., such as a reflective layer and/or a fluorescence enhancement layer) on a substrate. For example, the substrate of an array chip may itself be composed of a reflective material (e.g., such as a metal or a Bragg reflector), or it may be a base of substantially any coatable material that provides a solid support on which a fluorescent reflective layer can be disposed. The fluorescent reflective layer of the substrate may be made up of a thin, transparent, dielectric layer or a stack of thin, transparent, dielectric layers, where such dielectric materials include, but are not limited to, $SiO_2$, $TiO_2$, $Ta_2O_5$, $HfO_2$, $ZrO_2$, MgO, $Si_3N_4$, $MgF_2$ and $YF_3$.

In some embodiments, the sites on an array chip (e.g., such as sites in track regions and sites in field regions) may be defined by depressions or raised areas in the fluorescence reflective layer of the chip substrate. In such embodiments, the array chip sites may be between 30-1000 nm in width and/or length, and in a preferred aspect the sites may be 200-500 nm in width and/or length, even more preferably approximately 300 nm in width and/or length. In another specific aspect, the array chip sites may be separated by a distance of between 0.4 to 1.0 m.

The substrate layer(s) of the array chips described herein can be constructed using various multi-layer coating technologies. The optimization of the multilayer coating design can be done by applying one or more now-known or later-developed techniques. For example, a substrate base may be coated by any one of the following methods: thermal and/or electron beam vapor deposition, replication, transfer, film deposition, by processes of the CVD type (e.g., like LPCVD, PECVD etc.) or of the PVD type such as sputtering, (e.g., like DC magnetron sputtering). Ion-assisted deposition processes can be used as well as the sol-gel process. Substrate layers may be optionally transferred onto the substrate base by bonding or molecular adhesion.

In embodiments where depressions or raised areas in a fluorescence layer of an array chip substrate are desirable, multi-layer deposition on a reflective substrate base (or on a reflective layer through may be used to produce the desired structures. For example, a multilayer dielectric fluorescence layer can be designed using a layer of a material with a higher refractive index e.g., $Si_3N_4$ (having a refractive index of n=2.0), disposed on a dielectric material with a lower optical refractive index such as $SiO_2$ (n=148). Other coating materials, including multilayer coatings comprising more than two materials, can be used as well. In some embodiments, various structures may be constructed in the fluorescence layer in order to improve the detection of the fluorescence signals emitted from the material dispensed thereon; examples of such enhancement structures are described in U.S. patent application Ser. No. 12/261,447 filed on Oct. 30, 2008, the entire content of which is hereby incorporated by reference is fully set forth herein.

Etching can be provided by multiple available techniques, such as the damascene technique, whereby openings are selectively etched into a dielectric layer. Generally, a photoresist material is layered onto the dielectric layer and a pattern of openings is outlined in the photoresist layer using lithographic techniques. An anisotropic etch is then used to form the openings in the dielectric layer. The photoresist material is then removed. Where multiple layers and depths are desired, such a process requires the use of more than one mask layer with varying resistances to the anisotropic etch processes.

Imaging acquisition may be performed by methods known in the art, such as use of the commercial imaging package Metamorph. Data extraction may be performed by logic including a series of binaries written in, e.g., C/C++, and base-calling and read-mapping may be performed by a series of Matab and Pert scripts. During the process of imaging, as described herein quad-cell alignment based on the information encoded as the sites in the track regions of the array chip may be used to align the camera pixels of the imaging instrument with the sites on the array chip. The images from each cycle may be saved in a cycle directory, where the number of images is four times the number of frames. Cycle image data may then be saved into a directory structure organized for downstream processing.

Data extraction typically requires two types of image data: bright field images to demarcate the positions of all elements in the array chip; and sets of fluorescence images acquired during each cycle. The data extraction software identifies all objects with the bright field images, then for each such object, computes an average fluorescence value for each cycle. For any given cycle, there are four datapoints, corresponding to images taken at different wavelengths. These are consolidated, yielding a discontinuous read for each element. The extracted reads may then be matched against a reference by using various techniques and algorithms that can be performed by one or more computer systems.

While the present invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the claims and their equivalents that issue from the present application. The abstract and the title are not to be construed as limiting the scope of the present invention, as their purpose is to enable the appropriate authorities, as well as the general public, to quickly determine the general nature of the invention. In the claims that follow, unless the term. "means" is used, none of the features or elements recited therein should be construed as means-plus-function limitations pursuant to 35 U.S.C. §¶112, 6.

What is claimed is:

1. A device having a surface chemistry at experiment sites that binds and retains nucleic acid molecules, and a surface chemistry between the experiment sites that does not bind and retain nucleic acid molecules, wherein the device includes the following elements:
   a solid planar substrate having a surface with a length and a width, wherein both the length and the width are no less than 0.5 cm but not more than 10 cm in size;
   a two-dimensional array of experiment sites on the substrate that bind and retain nucleic acid molecules, the two-dimensional array being characterized as having a uniform distance between adjacent rows of experiment sites and between adjacent columns of experiment sites;
   a linear array of alignment sites on the substrate, wherein at least some of the alignment sites are experiment sites that bind and retain nucleic acid molecules, the linear array being characterized as having a uniform distance between adjacent alignment sites; and
   a site free band separating the two-dimensional array from the linear array;
   wherein the uniform distance between sites in the linear array is greater than and an integer multiple of the uniform distance between the rows and between the columns in the two-dimensional array.

2. A combination comprising a device according to claim 1 and a digital camera, wherein the device is optically aligned with the digital camera such that each experiment site in the two-dimensional array has a size that optically matches and is aligned with one pixel of the digital camera.

3. The device of claim 1, wherein the experiment sites in the two-dimensional array are arranged in a checkerboard pattern.

4. A combination comprising a planar device according to claim 1 and a digital camera, wherein the device is optically aligned with the digital camera such that
   each experiment site in the two-dimensional array has a size that optically matches and is aligned with four pixels of the digital camera.

5. The device of claim 1, wherein selected alignment sites in the linear array are deletion sites.

6. The device of claim 5, wherein the deletion sites are arranged within the linear array in accordance with a pseudo-random pattern.

7. The device of claim 1, wherein areas of the substrate other than said experiment sites and said alignment sites have been chemically treated to prevent binding of nucleic acid molecules.

8. The device of claim 1, wherein the linear array is oriented parallel to the length.

9. The device of claim 1, wherein the linear array is oriented parallel to the width.

10. The device of claim 1, further comprising a second linear array of alignment sites on the substrate, at which the surface of at least some of the alignment sites is configured to bind and retain nucleic acid molecules, wherein the second linear array is perpendicular to said first linear array of alignment sites.

11. The device of claim 1, comprising a plurality of two-dimensional arrays on the substrate, each two-dimensional array being 320-1,600 microns by 320-1,600 microns in size.

12. The device of claim 1, wherein the surface of the substrate is 2.5 cm by 7.5 cm.

13. The device of claim 1, comprising a plurality of two-dimensional arrays separated from each other on the substrate by linear arrays.

14. The chip device of claim 1, comprising at least sixteen two-dimensional arrays separated by each other on the substrate.

15. The chip device of claim 1, wherein adjacent experiment sites in the two-dimensional array are separated from each other by a distance of between 0.4 and 10 microns.

16. The chip device of claim 1, wherein the experiment sites are between 30 and 1000 nm in width and/or length.

17. The device of claim 1, comprising one billion sites that bind nucleic acid molecules arranged on the substrate in a plurality of fields each containing a two-dimensional array of experiment sites and a linear array of alignment sites.

* * * * *

UNITED STATES PATENT AND TRADEMARK OFFICE
CERTIFICATE OF CORRECTION

PATENT NO. : 9,880,089 B2
APPLICATION NO. : 14/090529
DATED : January 30, 2018
INVENTOR(S) : Bryan P. Staker and Paul Heilman Page 1 of 1

It is certified that error appears in the above-identified patent and that said Letters Patent is hereby corrected as shown below:

In the Claims

In Column 17, Line 1:
In Claim 14, delete "chip device" and
Insert -- device --.

In Column 17, Line 4:
In Claim 15, delete "chip device" and
Insert -- device --.

In Column 17, Line 7:
In Claim 29, delete "chip device" and
Insert -- device --.

Signed and Sealed this
Twenty-eighth Day of March, 2023

Katherine Kelly Vidal
*Director of the United States Patent and Trademark Office*